United States Patent
Herbst et al.

(10) Patent No.: US 6,395,140 B1
(45) Date of Patent: May 28, 2002

(54) METHOD FOR PRODUCING (METH)ACRYLIC ACID

(75) Inventors: Holger Herbst, Frankenthal; Gerhard Nestler, Ludwigshafen; Ulrich Hammon, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/529,995

(22) PCT Filed: Oct. 21, 1998

(86) PCT No.: PCT/EP98/06678

§ 371 (c)(1),
(2), (4) Date: Apr. 24, 2000

(87) PCT Pub. No.: WO99/20594

PCT Pub. Date: Apr. 29, 1999

(30) Foreign Application Priority Data

Oct. 22, 1997 (DE) .......................................... 197 46 689

(51) Int. Cl.⁷ .......................... B01D 3/34; C07C 51/44; C07C 51/50; C07C 57/04
(52) U.S. Cl. ............................. 203/8; 203/49; 203/78; 203/80; 203/99; 203/DIG. 19; 562/600
(58) Field of Search ....................... 203/99, 8, DIG. 19, 203/DIG. 21, 49, 51, 52, 3, 78, DIG. 16, 73, 80; 562/600; 159/16.1, 47.1

(56) References Cited

U.S. PATENT DOCUMENTS

| 3,666,794 | A | * | 5/1972 | Otsuki et al. ............... 562/600 |
| 3,951,756 | A | * | 4/1976 | Dirks et al. ........... 203/DIG. 21 |
| 4,369,097 | A | * | 1/1983 | Nezu et al. ..................... 203/8 |
| 4,599,144 | A | * | 7/1986 | Baleiko et al. ...... 203/DIG. 19 |
| 5,637,222 | A | * | 6/1997 | Herbst et al. ................ 210/634 |
| 5,961,790 | A | * | 10/1999 | Herbst et al. ................ 562/600 |
| 5,968,322 | A | * | 10/1999 | Arnoldy et al. ................ 203/49 |

FOREIGN PATENT DOCUMENTS

| DE | 38 37 955 A | 5/1989 |
| DE | A 43 08 087 | 9/1994 |
| DE | A 44 36 243 | 4/1996 |
| EP | 0 717 029 A | 6/1996 |
| EP | 0 722 925 A | 7/1996 |

* cited by examiner

Primary Examiner—Virginia Manoharan
(74) Attorney, Agent, or Firm—Oblon, Spivak, McClelland, Maier & Neustadt, P.C.

(57) ABSTRACT

In a process for the preparation of (meth)acrylic acid from a mixture which contains (meth)acrylic acid and a solvent having a boiling point above the boiling point of (meth) acrylic acid by distillation of the mixture in a column which is connected to an evaporator and has a stripping section and a rectifying section, between which the mixture is fed in, and a side take-off for the (meth)acrylic acid, a polymeization inhibitor is fed into the column in the region of the top of the column and in the region of the side take-off, that amount of polymerization inhibitor which is introduced in the region of the top of the column being smaller than the amount introduced in the region of the side take-off.

9 Claims, No Drawings

METHOD FOR PRODUCING (METH)ACRYLIC ACID

The present invention relates to a process for the preparation of (meth)acrylic acid from a mixture which contains (meth)acrylic acid and solvents having a boiling point above the boiling point of (meth)acrylic acid.

(Meth)acrylic acid is used as abbreviated notation and represents acrylic acid or methacrylic acid. (Meth)acrylic acid, either as the acid or in the form of its esters, is particularly important in the preparation of polymers for a very wide range of applications, for example as adhesives, textile assistants or aqueous coating dispersions.

(Meth)acrylic acid is prepared, as a rule, by catalytic gas-phase oxidation of alkanes, alkanols, alkenes or alkenals which contain 3 or 4 carbon atoms. (Meth)acrylic acid is particularly advantageously obtainable, for example, by catalytic gas-phase oxidation of propene, acrolein, tert-butanol, isobutene or methacrolein.

These starting materials in gaseous form are as a rule diluted with inert gases, such as nitrogen, $CO_2$, saturated hydrocarbons and/or steam, are passed as a mixture with oxygen, at elevated temperatures (usually from 200 to 400° C.), and, if required, superatmospheric pressure, over mixed oxide catalysts and oxidized to (meth)acrylic acid.

Owing to the numerous simultaneous and subsequent reactions taking place in the course of the catalytic gas-phase oxidation and because of the required inert diluent gases, however, it is not pure (meth)acrylic acid which is obtained in the catalytic gas-phase oxidation but a reaction mixture which essentially contains (meth)acrylic acid, the inert diluent gases and by-products. For example, the reaction mixture obtained in the oxidation of propene contains, inter alia, acetic acid, propionic acid, maleic acid anhydride, aldehydes, propane, water, carbon oxides, nitrogen and oxygen in addition to acrylic acid.

The isolation of the (meth)acrylic acid from the reaction mixture is essentially carried out by passing the reaction gases countercurrent to a descending absorption liquid in a conventional absorption column, then substantially removing the readily volatile secondary components, by stripping in a desorption column, from the liquid discharge of the absorption column, which is composed essentially of (meth)acrylic acid, the absorbent and secondary components, and then separating the liquid discharge of the desorption column for isolating the (meth)acrylic acid and sparingly volatile secondary components in a column by distillation.

The (meth)acrylic acid is usually isolated by feeding the mixture into a column having a rectifying section and a stripping section, a part of the residual low boilers, mainly acetic acid, being taken off by the top of the column, the (meth)acrylic acid being isolated via a side take-off and the absorbent and high-boiling by-products being obtained in the bottom product.

Such a process is described in DE-A 44 36 243. The (meth)acrylic acid can also be taken off via the top, as described in DE-A 43 08 087. In all working-up steps, stabilizers, for example phenothiazine for (meth)acrylic acid, are added to the product. The addition of the polymerization inhibitors is necessary since (meth)-acrylic acid has a high tendency to polymerize, especially under thermal load. Since the polymers are as a rule insoluble, polymerization results in blockage of lines, evaporator pipes, etc. and hindrance of the distillation owing to deposits on the column trays. For this reason, large amounts of inhibitor are used. A pure (meth)acrylic acid can be obtained from the resulting crude (meth)acrylic acid by means of further purification steps, for example crystallization. The crude (meth)acrylic acid has, as a rule, a purity of from 80 to 99% by weight and the pure (meth)acrylic acid has, as a rule, a purity of at least 99.7% by weight.

In the further processing of the (meth)acrylic acid, for example in the purification by crystallization, the large amount of inhibitor does however present problems. In the crystallization, the (meth)acrylic acid is separated out by freezing while the impurities and the polymerization inhibitors remain in solution and are inevitably concentrated. Since some of the conventional inhibitors, for example phenothiazine, have only a low solubility (meth)acrylic acid, the solubility limit is rapidly exceeded at low temperatures so that the polymerization inhibitor is precipitated as a solid and contaminates the (meth)acrylic acid separated out by freezing.

It is an object of the present invention to provide a process for the isolation of (meth)acrylic acid by distillation from a mixture which contains (meth)acrylic acid and a high-boiling inert absorbent (solvent), in which a (meth)acrylic acid having a low polymerization inhibitor content is obtained in a rectification column via a side take-off, the column nevertheless being sufficiently stabilized, i.e. the running times being long, and the (meth)acrylic acid obtained having a sufficient shelf-life.

We have found that this object is achieved, according to the invention, by providing a process for the preparation of (meth)acrylic acid from a mixture which contains (meth)acrylic acid and a solvent having a boiling point above the boiling point of (meth)acrylic acid by distillation of the mixture in a column which is connected to an evaporator and has a stripping section and a rectifying section, between which the mixture is fed in, and a side take-off for the (meth)acrylic acid, wherein a polymerization inhibitor is fed into the column in the region of the top of the column and in the region of the side take-off, that amount of polymerization inhibitor which is introduced in the region of the top of the column being smaller than the amount introduced in the region of the side take-off.

Preferably, the amount of polymerization inhibitor introduced in the region of the top of the column is chosen so that said polymerization inhibitor is present in a concentration of from 5 to 500 mg/l in the reflux between the top of the column and the side take-off, and the amount of polymerization inhibitor introduced in the region of the side take-off is chosen so that said polymerization inhibitor is present in a concentration of from 100 to 10,000 mg/l in the reflux between side take-off and evaporator and in at least twice the concentration compared with the region between the top of the column and the side take-off.

At least a part of the top product is recycled to the column in the region of the top of the column and at least a part of the (meth)acrylic acid removed from the side take off is recycled to the column in the region of the side take-off after the addition of the polymerization inhibitor.

The term solvent is to be understood as meaning a high-boiling inert organic absorbent whose boiling point at atmospheric pressure (1 atm) is above the boiling point of (meth)acrylic acid and preferably above 161° C.

Suitable solvents are described, for example, in DE-A 21 36 396, DE-A 22 41 714 and DE-A 43 08 087. Examples are middle oil fractions from paraffin distillation, ethylhexanoic acid, N-methylpyrrolidone, dialkyl phthalate, diphenyl ether, biphenyl or mixtures of the stated liquids, for example mixtures of biphenyl, diphenyl ether and, if required, o-dimethyl phthalate.

The isolation of the (meth)acrylic acid by distillation is carried out in a column which consists of a stripping section and a rectifying section with side take-off, side take-off being present roughly in the middle third, preferably just below the upper third of the rectifying section. The rectification unit preferably consists of a stripping section having from 3 to 15 trays and a rectifying section having from 15 to 50 trays. The mixture to be separated is fed in between the upper end of the stripping section and the lower end of the rectifying section. The (meth)acrylic acid is separated off via a side take-off which is present in particular in the rectifying section below the 5th to 15th tray, counting from the top of the column. The side take-off product is removed in liquid form, a part thereof being recycled to the column, below the side take-off (lower reflux). One or more evaporators in the possible technical embodiments known to a person skilled in the art are present at the lower end of the stipping section. At the top of the rectifying section, the vapors are condensed with the aid of one or more condensers in the technical embodiments known to a person skilled in the art. A part of the condensed vapors is recycled to the top of the column (upper reflux).

Suitable rectification columns for the process according to the invention are all conventional types. The rectification column may be, for example, a tray column or a packed column. Tray columns are preferably used. Examples are valve-tray columns, bubble-cap columns, tunnel-cap columns, sieve-tray columns and dualflow tray columns.

Very generally, the novel isolation of (meth)acrylic acid by rectification is preferably carried out at reduced pressure. The procedure is advantageously carried out at a top pressure of ≦500, usually from 10 to 200, preferably from 10 to 100, mbar. In a corresponding manner, the associated temperatures in the bottom of the rectification column are as a rule from 100 to 230° C. and those at the top of the column are from 30 to 80° C.

The separation line between rectifying section and stripping section of the rectification column is advantageously about at the end of the first third of the distance between the lowest and highest theoretical plate. The side take-off is preferably located in the upper third of the rectifying section.

The polymerization inhibitor used for preventing polymerization of the (meth)acrylic acid in the rectification column is, for example, hydroquinone, hydroquinone monomethyl ether, paranitrosophenol, paramethoxyphenol or phenothiazine or a mixture thereof, preferably phenothiazine, preferably dissolved in (meth)acrylic acid.

The inhibitor solution is fed in at two points:
1. At the top of the column, directly or mixed with the upper reflux, the inhibitor concentration in the liquid phase on the column trays between the side take-off and the top usually being from 5 to 500, particularly from 10 to 300, preferably from 20 to 150, mg/l. Accordingly, the (meth)acrylic acid removed by the side take-off contains the inhibitor concentration as set above.
2. Immediately below the side take-off, directly or mixed with the lower reflux, the inhibitor concentration in the liquid phase on the column tray between the side take-off and the bottom usually being from 100 to 10,000, particularly from 100 to 5000, preferably from 300 to 1000, mg/l.

The effect of the inhibitor metered in can be supported or supplemented by feeding oxygen, preferably in the form of air, to the evaporator and/or to the column.

The advantages of this novel procedure are:
The inhibitor concentration can be varied from top to bottom in the column. In the upper column section, where there is a lower thermal load, it is possible to use a lower inhibitor concentration than in the lower part of the column, where the thermal load is higher.

In this way, the inhibitor costs can be reduced.

The inhibitor concentration in the acrylic acid obtained in the side take-off can thus be set so low that it does not interfere in the further processing of the acid, for example in the further purification by crystallization.

Inhibitors used in the upper part of the column may differ from those in the lower part of the column, where, owing to the higher temperatures, it is necessary to use inhibitors having higher heat stability.

The mixture which contains (meth)acrylic acid and the solvent can, for example, be obtained by
(a) catalytic gas-phase oxidation of alkanes, alkanols, alkenes and/or alkenals of 3 or 4 carbon atoms to give a gas mixture containing (meth)acrylic acid,
(b) bringing the gas mixture obtained in (a) into contact with the solvent in an absorption column to absorb the (meth)acrylic acid in the solvent,
(c) stripping the mixture obtained in (b) in a desorption column to remove readily volatile by-products.

The more detailed procedure is described at the outset.
The examples which follow illustrate the invention.

EXAMPLE 1

A reaction mixture containing acrylic acid was produced by catalytic gas-phase oxidation of acrolein according to Example B1 of DE-A 43 02 991. 2.1 m$^3$ (S.T.P.)/l of this reaction mixture were cooled to 170° C. in a gas cooler (Quench) by injecting a coolant mixture comprising 57.4% by weight of diphenyl ether, 20.7% by weight of biphenyl and 20% by weight of o-dimethyl phthalate.

That portion of the coolant which had remained liquid was then separated from the gas phase consisting of reaction gas and vaporized coolant in a separator. The gas phase at 170° C. was passed, below the first tray, into a bubble-cap column having 27 trays and exposed to a countercurrent of 3 l/h of the absorbent, likewise composed of 57.4% by weight of diphenyl ether, 20.7% by weight of biphenyl and 20% by weight of dimethyl phthalate and added at the top of the column at 45° C. The discharge from the absorption column was heated indirectly to 150° C. in a heat exchanger and added to the top of a desorption column which was in the form of a bubble-cap column having 20 trays. In the desorption column, components which were low-boiling compared with acrylic acid, e.g. acetic acid and aldehydes, were substantially removed from the mixture by stripping with nitrogen (400 l/h, countercurrent). The discharge from the desorption column contained 14.7% by weight of acrylic acid.

This discharge was passed at 25° C. in an amount of 3 l/h into a rectification column which comprised 20 bubble caps and through which air flowed, between the fifth and sixth tray (considered from the evaporator). The rectification column was operated at a bottom temperature of 160° C. and a bottom pressure of 130 mbar and a top pressure of 80 mbar.

1400 ml/hour of liquid acrylic acid having a purity of 99.7% by weight were removed continuously via a side take-off between the fifteenth and sixteenth tray (considered from the evaporator). The top product in vapor form was condensed (600 ml/h), phenothiazine (0.01 g/l) was added as a polymerization inhibitor and, apart from 50 ml/h, said top product was recycled to the rectification column, above the top bubble cap.

The top product removed (50 ml/h) was added again to the discharge of the absorption column.

In addition, 960 ml/h of the acrylic acid removed were mixed with 0.05 g/l of phenothiazine and fed in directly below the side take-off, so that a concentration of about 500 ppm resulted between the side take-off and the feed point of the column.

The acrylic acid obtained contained 105 ppm of phenothiazine, and it was not until after an operating time of 410 hours that the operation of the rectification column had to be stopped owing to soiling of the stripping section and of the evaporator. No polymer occurred in the rectifying section.

COMPARATIVE EXAMPLE C1

The procedure was as in Example 1, except that 0.06 g/l of phenothiazine was added to the reflux to the top of the column so that a concentration of about 500 ppm resulted between the top and the feed point of the column. No additional inhibitor was added below the side take-off. After an operating time of 190 hours, the operation of the column had to be stopped owing to soiling of the stripping section. The acrylic acid isolated contained 550 ppm of phenothiazine.

COMPARATIVE EXAMPLE C2

The procedure was as in Comparative Example 1. However, 0.01 g/l of phenothiazine was added to the reflux to the top of the column so that a concentration of about 100 mg/l resulted.

The acrylic acid removed contained 110 ppm of phenothiazine and the operating time of the distillation was only 90 hours.

We claim:

1. A process for the preparation of (meth)acrylic acid from a mixture which contains (meth)acrylic acid and a solvent having a boiling point above the boiling point of (meth)acrylic acid by distillation of the mixture in a column which is connected to an evaporator and has a stripping section and a rectifying section, between which the mixture is fed in, and a side take-off for the (meth)acrylic acid, wherein a polymerization inhibitor is fed into the column in the region of the top of the column and in the region of the side take-off, that amount of polymerization inhibitor which is introduced in the region of the top of the, column being smaller than the amount introduced in the region of the side take-off, and wherein the amount of polymerization inhibitor introduced in the region of the top of the column is chosen so that said polymerization inhibitor is present in a concentration of from 5 to 500 mg/l in the reflux between the top of the column and the side take-off, and the amount of polymerization inhibitor introduced in the region of the side take-off is chosen so that said polymerization inhibitor is present in a concentration of from 100 to 10,000 mg/l in the reflux between side take-off and evaporator and in at least twice the concentration compared with the region between the top of the column and the side take-off.

2. A process as claimed in claim 1, wherein the polymerization inhibitor used is hydroquinone, hydroquinone monomethyl ether, paranitrosophenol, paramethoxyphenol, phenothiazine or a mixture thereof.

3. A process as claimed in claim 1, wherein the solvent has a boiling point higher than 161° C.

4. A process as claimed in claim 1, wherein oxygen is fed to the evaporator or to the column.

5. A process as claimed in claim 1, wherein the distillation is carried out at reduced pressure.

6. A process as claimed in claim 1, wherein the solvent is a mixture of diphenyl ether, biphenyl and, optionally, o-dimethyl phthalate.

7. A process as claimed in any of claims 1 to 6, wherein the mixture which contains (meth)acrylic acid and the solvent is obtained by
   (a) catalytic gas-phase oxidations of alkanes, alkanols, alkenes or alkenals of 3 or 4 carbon atoms to give a gas mixture containing (meth)acrylic acid,
   (b) bringing the gas mixture obtained in (a) into contact with the solvent in an absorption column to absorb the (meth)acrylic acid in the solvent,
   (c) stripping the mixture obtained in (b) in a desorption column to remove readily volatile by-products.

8. A process for the preparation of (meth)acrylic acid from a mixture which contains (meth)acrylic acid and a solvent having a boiling point above the boiling point of (meth)acrylic acid by distillation of the mixture in a column which is connected to an evaporator and has a stripping section and a rectifying section, between which the mixture is fed in, and a side take-off for the (meth)acrylic acid, wherein a polymerization inhibitor is fed into the column in the region of the top of the column and in the region of the side take-off, that amount of polymerization inhibitor which is introduced in the region of the top of the column being smaller than the amount introduced in the region of the side take-off, wherein the amount of polymerization inhibitor introduced in the region of the top of the column is present in a concentration of from 5 to 500 mg/l in the reflux between the top of the column and the side take-off, and the amount of polymerization inhibitor introduced in the region of the side take-off is present in a concentration of from 100 to 10,000 mg/l in the reflux between side take-off and evaporator and in at least twice the concentration compared with the region between the top of the column and the side take-off, and wherein at least a part of the top product is recycled to the column in the region of the top of the column and at least a part of the (meth)acrylic acid removed from the side take-off is recycled to the column in the region of the side take-off after the addition of the polymerization inhibitor.

9. A process for the preparation of (meth)acrylic acid from a mixture which contains (meth)acrylic acid and a solvent having a boiling point above the boiling point of (meth)acrylic acid by distillation of the mixture in a column which is connected to an evaporator and has a stripping section and a rectifying section, between which the mixture is fed in, and a side take-off for the (meth)acrylic acid, wherein a polymerization inhibitor is fed into the column in the region of the top of the column and in the region of the side take-off, that amount of polymerization inhibitor which is introduced in the region of the top of the column being smaller than the amount introduced in the region of the side take-off, wherein at least a part of the top product is recycled to the column in the region of the top of the column and at least a part of the (meth)acrylic acid removed from the side take-off is recycled to the column in the region of the side take-off after the addition of the polymerization inhibitor.

* * * * *